United States Patent [19]

Desruelles

[11] Patent Number: 5,329,561
[45] Date of Patent: Jul. 12, 1994

[54] DEVICE FOR CHECKING THE THICKNESS AND THE COHESION OF THE INTERFACE OF A DUPLEX TUBE

[75] Inventor: Didier Desruelles, Gresy-sur-Isere, France

[73] Assignees: Framatome; Cogema; Societe en nom Collectif Zircotube, all of France

[21] Appl. No.: 16,890

[22] Filed: Feb. 12, 1993

Related U.S. Application Data

[62] Division of Ser. No. 711,997, Jun. 7, 1991, Pat. No. 5,225,148.

[30] Foreign Application Priority Data

Jun. 8, 1990 [FR] France .................. 90 07187

[51] Int. Cl.$^5$ ......................................... G21C 17/017
[52] U.S. Cl. ................................. 376/245; 73/588; 73/622; 324/226
[58] Field of Search .............. 376/245, 249, 252, 291, 376/292; 73/588, 601, 622, 625; 324/220, 222, 226; 33/502

[56] References Cited

U.S. PATENT DOCUMENTS

| | | | |
|---|---|---|---|
| 3,375,706 | 4/1968 | Pandelis et al. | 73/679 |
| 3,568,051 | 3/1971 | Vild | 324/37 |
| 3,886,793 | 6/1975 | Cramer et al. | 73/167 |
| 4,391,143 | 7/1983 | Cook et al. | 73/623 |
| 4,741,878 | 5/1988 | Gebelin et al. | 376/248 |
| 4,814,703 | 3/1989 | Carr et al. | 324/207 |
| 4,856,337 | 8/1989 | Metala et al. | 73/601 |
| 4,955,235 | 9/1990 | Metala et al. | 73/601 |
| 5,025,215 | 6/1991 | Pirl | 324/220 |
| 5,113,358 | 5/1992 | Reber | 364/563 |
| 5,145,637 | 9/1992 | Richardson et al. | 376/249 |

FOREIGN PATENT DOCUMENTS

| | | | |
|---|---|---|---|
| 464826 | 1/1992 | European Pat. Off. | 324/222 |
| 61-292549 | 12/1986 | Japan | 324/222 |

OTHER PUBLICATIONS

Renken, C. J. and R. H. Selner, "Refractory Metal Tubing Inspection Using Ultrasonic and Pulsed Eddy Current Methods", *Materials Evaluation*, May 1966, pp. 257–262.

*Primary Examiner*—Peter A. Nelson
*Assistant Examiner*—Chrisman D. Carroll
*Attorney, Agent, or Firm*—Pollock, Vande Sande & Priddy

[57] ABSTRACT

The duplex tube (1) comprises a tubular core (2) and a cladding or covering layer (3) made from an alloy, the base metal of which is identical to the base metal of the alloy constituting the tubular core (2). Ultrasonic waves at normal incidence are emitted into the thickness of the covering (3) and of the core (2) of the tube (1), the ultrasonic waves reflected by the inner and outer surfaces of the tube, by its interface (4) and by any flaws in cohesion at the interface (4) are collected, the propagation times of the ultrasonic waves in the thickness of the tube (1) are measured, the amplitude and the shape of the reflected waves is determined, the tube (1), from its outer surface, is subjected to a magnetic induction created by a multi-frequency sinusoidal current, measurements of the phase and/or amplitude of the currents induced in the tube (1) are made, the thickness of the covering layer (3) is deduced therefrom, the total thickness of the tube (1) is calculated from the measurements of the propagation times of the ultrasonic waves and of the thickness of the covering layer (3), and the cohesion of the tube at its interface (4) is determined by analyzing the amplitude and the shape of the ultrasonic waves reflected by the interface (4) or transmitted by the covering layer (3).

6 Claims, 3 Drawing Sheets

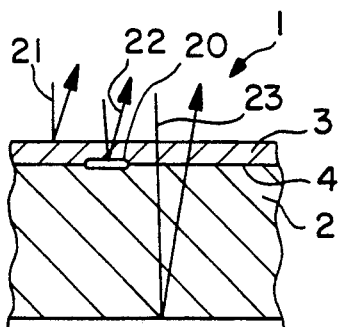
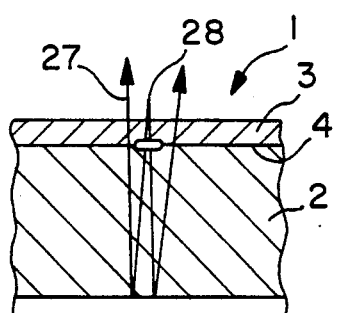
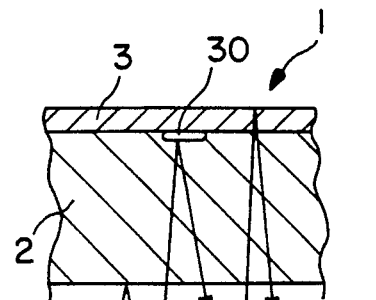
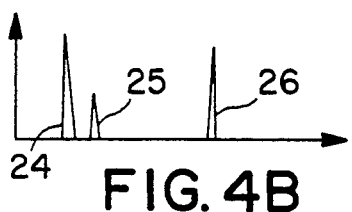
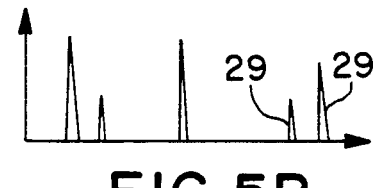
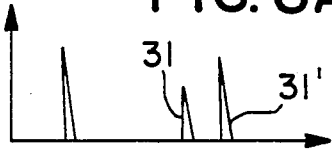
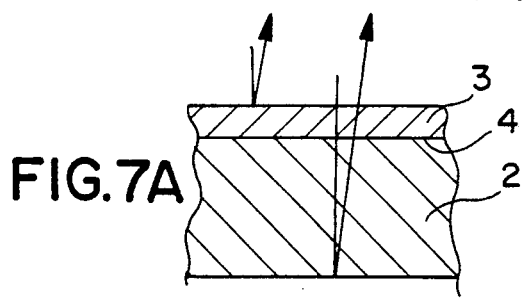
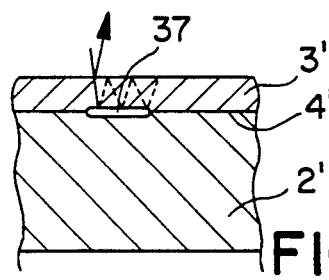
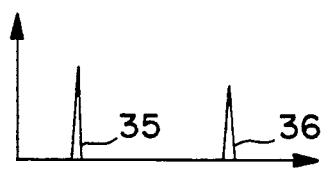
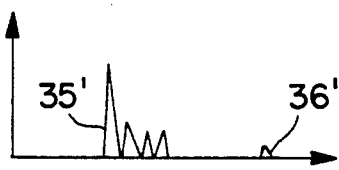
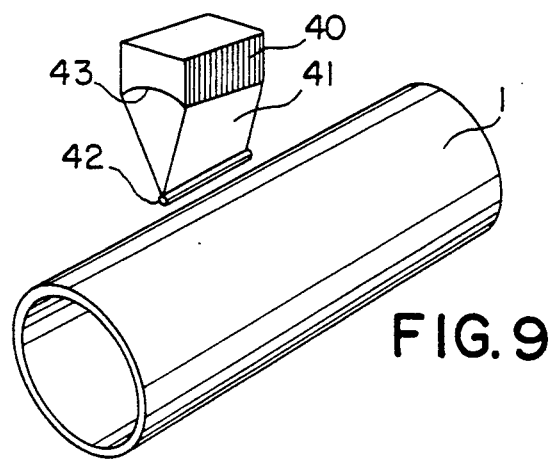

DEVICE FOR CHECKING THE THICKNESS AND THE COHESION OF THE INTERFACE OF A DUPLEX TUBE

This is a Division of application Ser. No. 07/711,997, filed Jun. 7, 1991, now U.S. Pat. No. 5,225,148.

FIELD OF THE INVENTION

The invention relates to a device for checking the thickness and the cohesion of the interface of a duplex tube, and in particular of a zirconium alloy duplex tube used as a jacket element for a fuel rod of an assembly for a water-cooled nuclear reactor.

BACKGROUND OF THE INVENTION

The fuel assemblies of water-cooled nuclear reactors, and in particular of pressurized-water nuclear reactors, comprise a framework into which are introduced fuel rods consisting of a Jacket enclosing a nuclear combustible material such as uranium or plutonium oxide in the form of sintered pellets.

The Jacket made from a zirconium alloy tube must have a good resistance to corrosion under the effect of the primary fluid circulating in contact with the outer surface of the Jacket.

In order to constitute the Jacket of the fuel rods of the assemblies of water-cooled reactors, use is usually made of a zirconium-based alloy containing mainly tin and iron.

In order to improve the corrosion stability under irradiation of the Jackets of fuel rods in the operating environment of the nuclear reactor, and thus to increase the lifetime of the fuel assemblies in the core, modifications or adjustments have been proposed to the composition of these zirconium alloys, or alternatively it has been proposed to replace these alloys containing tin, iron and chromium with alloys containing other elements such as vanadium, niobium or copper.

It has also been proposed, for example in EP-A-0,212,351, to produce the Jacket in the form of a duplex tube comprising a tubular inner core made from a zirconium alloy of a conventional type such as that described above, and a surface layer consisting of a cladding or a covering improving the corrosion stability of the Jacket.

The zirconiumalloy constituting the cladding or covering layer differs from the alloy constituting the core of the tube and contains iron and at least one of the elements vanadium, platinum and copper. This surface layer, the thickness of which represents 5 to 20% of the total thickness of the wall of the jacket, can be produced by extrusion of a billet consisting of an inner tube made from zirconiumalloy of a conventional composition over which is fitted an outer tube having the composition of a surface layer.

The jacket is then rolled in a pilgrim step rolling mill to its final diameter.

More recently, there has been proposed in FR-A-89-00761 filed jointly by the companies FRAMATOME, COGEMA, CEZUS and ZIRCOTUBE, a duplex tube, the surface layer of which, having a thickness lying between 10 and 25% of the total thickness of the wall of the Jacket, consists of a zirconium-based alloy containing tin, iron and niobium or vanadium. The tubular core of the duplex tube can be made from a conventional zirconium alloy in the case of the manufacture of the Jackets for fuel rods, or from a zirconiumbased alloy containing mainly niobium as the alloying element.

In all cases, it is necessary to ensure the perfect quality of the duplex tubes which are intended to constitute Jackets for fuel rods, in particular in terms of the diameter of the tube, the total thickness of the Jackets, the thickness of the outer cladding layer and the cohesion of the interface zone between the cladding layer and the core of the tube.

Checks must be carried out at the factory on very large quantities of tubes, the diameter of which is very small as compared to the length.

The checking of the diameter and the total thickness of the jacket can be carried out by using a conventional technique consisting in measuring the distance in the propagation times of pulse-shaped ultrasonic waves which are reflected by the outer surface and by the inner surface of the tube.

This ultrasonic checking and measuring technique, known under the name of the "pulse-echo" technique, may be adapted in order to take account of the cladding layer in the calculation of the total thickness of the jacket.

It has also been proposed to use a technique using ultrasonic waves in order to check the thickness of the cladding of a duplex tube based on zirconium alloy.

This technique, described in FR-A-2,629,586 filed in the name of the company CEZUS, employs an ultrasonic-wave check adapted to the measurement of a layer of small thickness, the acoustic properties of which are very similar to those of the core of the tube of greater thickness.

This improved technique does not, however, permit the measurement of cladding thicknesses of less than 0.4 mm, inasmuch as the industrial implementation of the method under satisfactory conditions requires the use of ultrasonic waves whose frequency does not exceed 20 MHz.

In the case of a cladding layer whose thickness lies between 80 and 100 $\mu$m, which corresponds to the conditions encountered most commonly in the case of duplex tubes used as Jacket material, it would be necessary to employ ultrasonic waves at very high frequencies (for example of the order of 100 MHz), which makes it extremely difficult to apply the method in an industrial context.

Furthermore, in the case of jackets for fuel rods, the cladding layer and the tubular core of the duplex tube consist of very slightly alloyed zirconiumbased alloys which have very similar acoustic properties, with the result that the coefficient of reflection of the acoustic waves at the cladding/core interface is very small (generally less than 2%). The interface echo is then very small and becomes drowned out in the acoustic and electronic noise of the ultrasonic signal.

A measurement method and apparatus have been proposed in FR-A-2,534,015 which make it possible to determine the thickness of a zirconium covering on a zirconium-alloy tube, employing the analysis and the measurement of currents induced in the cladding layer of the duplex tube, by magnetic induction, using an exciting current the frequency of which is selected as a function of the nominal thickness of the cladding or covering layer of the tube.

The frequency selected and the processing of the signals corresponding to the induced currents likewise make it possible to eliminate, to a certain degree, the measurement errors resulting from a variation in the width of the air gap between the exciting coil and the wall of the tube.

This technique, which is relatively complex to implement, does not make it possible, however, to compensate for the variations in the conductivity of the material constituting the core of the tube and the variations in the conductivity of the material constituting the cladding.

Furthermore, this technique does not make it possible to check independently the total thickness of the tube and the cohesion of the interface zone between the cladding or covering layer of the tube and the tubular core.

SUMMARY OF THE INVENTION

The object of the invention is to provide a device for checking the thickness and the cohesion of the interface of a duplex tube comprising a tubular core made from an alloy such as a zirconium alloy and covered with a covering or cladding layer made from an alloy the base metal of which is identical to the base metal of the alloy constituting the tubular core, this device making it possible to check the geometrical dimensions of the duplex tube and, in particular, its total thickness, and the thickness of the covering and cladding layer, and to detect flaws in cohesion at the interface between the covering or cladding layer and the tubular core.

To this end, for various measuring and checking zones, around the circumference or along the length of the tube, the following operations are carried out continuously or discontinuously:

- ultrasonic waves are emitted in such a way that these waves are propagated in the covering and in the core of the tube in substantially radial directions,
- the ultrasonic waves reflected by the inner and outer surfaces of the tube, by its interface between the core and the covering and by any flaws in cohesion at the interface, or transmitted by the covering or cladding layer, are collected,
- the propagation time of the ultrasonic waves in the thickness of the tube is measured,
- the amplitude and shape of the reflected waves is determined,
- the tube is subjected, from its outer surface, to a magnetic induction created by a multi-frequency sinusoidal current,
- measurements are taken of the phase and/or amplitude of the currents induced in the tube, termed Foucault currents,
- the thickness of the covering layer is deduced therefrom,
- the total thickness of the tube is calculated from the measurements of the propagation times of the ultrasonic waves and of the thickness of the covering layer, and
- the cohesion of the tube at its interface is determined by analyzing the amplitude and the shape of the ultrasonic waves reflected by the interface or transmitted by the covering or cladding layer.

BRIEF DESCRIPTION OF THE DRAWINGS

In order to make the invention readily comprehensible, several embodiments of the invention will now be described by way of example and with reference to the accompanying drawings.

FIGS. 4A and 4B, 5A and 5B and 6A and 6B respectively are views similar to FIGS. 2A and 2B showing the implementation of the method for detecting flaws in cohesion at the interface between the covering or cladding layer and the core of a duplex tube by an ultrasonic technique, according to three known alternatives.

FIGS. 7A and 7B, and FIGS. 8A and 8B are views similar to FIGS. 2A and 2B respectively showing the implementation of a method for detecting flaws at the interface between a covering or cladding layer and the metallic core of a duplex tube by an ultrasonic transmission technique, according to the invention.

FIGS. 7A and 7B relate to a zone of a tube having no interface flaws.

FIGS. 8A and 8B relate to a zone of a tube having an interface flaw and to its detection by the transmission of ultrasonic waves.

FIG. 9 is a perspective view of a device for ultrasonic detection of the flaws of the interface of a duplex tube.

DESCRIPTION OF THE PREFERRED EMBODIMENTS

Figure 1:
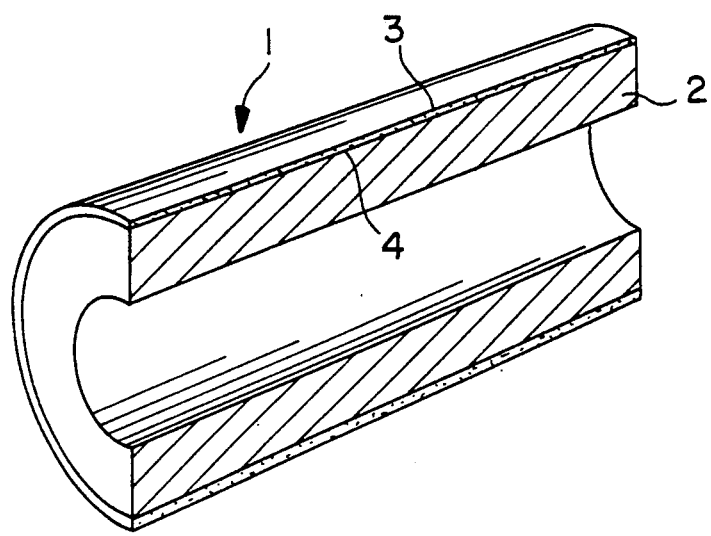
FIG. 1 is an exploded perspective view of part of a duplex tube used as a Jacket element for a fuel rod.

As shown in FIG. 1, a duplex tube 1 comprises a tubular core 2 made from a zirconium alloy covered externally by a cladding layer 3 made from a second zirconium alloy, the composition of which differs from the composition of the alloy constituting the core 2.

The zirconium alloys constituting the core 2 and the cladding layer 3 of the duplex tube 1 are low-alloy zirconium alloys in which the content of alloying elements is less than 1% by weight for each of these elements.

The tubular core 2 and the cladding layer 3 therefore have acoustic properties which are extremely similar to each other. Furthermore, the covering or cladding layer 3 has a small thickness, generally between 60 and 80 $\mu$m, the metallic core 2 itself having a thickness slightly less than 600 $\mu$m.

A duplex tube such as that shown in FIG. 1, used as a jacket for a fuel rod of a pressurized-water nuclear reactor assembly, generally has an external diameter of the order of 10 mm and a length of the order of 4 m.

Figure 2A:
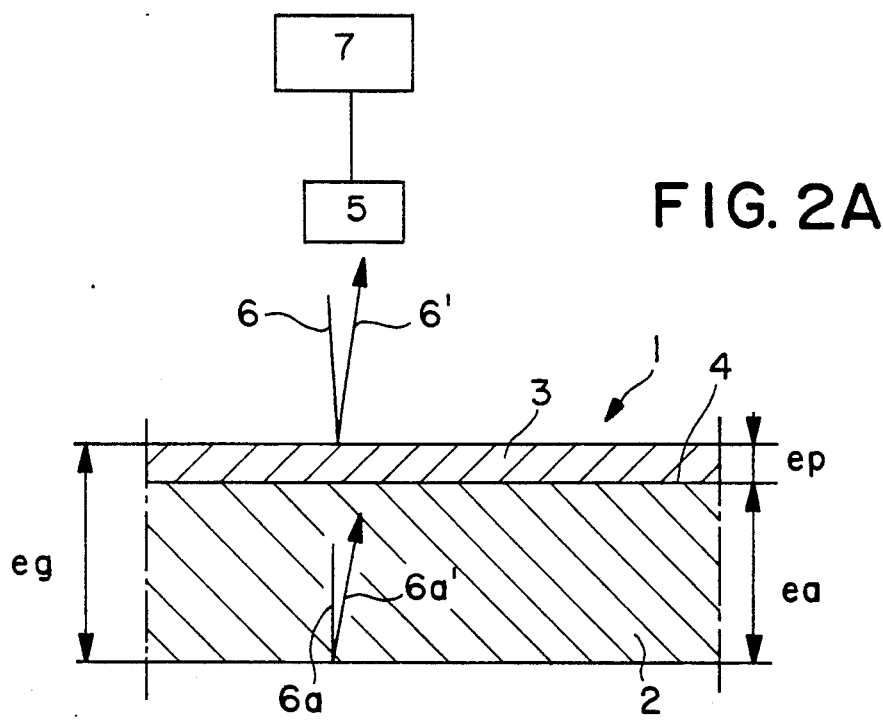
FIG. 2A is a sectional view of the wall of a duplex tube showing schematically the implementation of a method for measuring thickness from the propagation times of ultrasonic waves in the wall of the tube.

In FIG. 2A, the wall of a duplex tube such as that shown in FIG. 1 has been shown in section, comprising a tubular core 2 covered by a cladding and covering layer joined to the metallic core along a cylindrical interface surface 4.

In order to measure the total thickness of the wall of the Jacket consisting of the core 2 and the cladding layer 3, an ultrasonic transducer 5 is used which emits an ultrasonic-wave beam in the direction of the outer surface of the duplex tube, consisting of the outer surface of the cladding layer 3.

The tube 1 is immersed in a coupling medium consisting of a liquid permitting the transmission of the ultrasonic waves emitted by the transducer 5.

Part of the ultrasonic-wave beam 6 is reflected by the outer surface of the duplex tube in the form of a beam 6' which is collected by the transducer 5 and converted into an electrical signal which is transmitted to a processing unit 7.

The corresponding echo 8 can be displayed on an oscillogram giving an image of its amplitude and of its position against a time scale.

The ultrasonic beam 6a transmitted through the wall of the duplex tube is reflected, in the form of a beam 6'a, by the inner surface of the core 2 of the duplex tube.

Figure 2B:
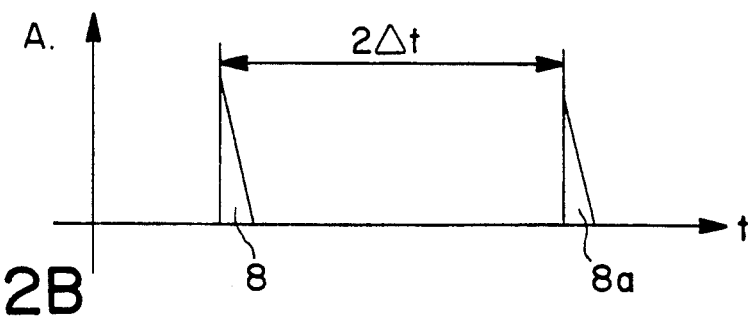
FIG. 2B is a diagram giving the amplitude of the ultrasonic waves reflected by the walls of the tube shown in FIG. 2A as a function of time.

The ultrasonic beam 6'a is collected by the transducer 5 which converts it into an electrical signal and enables it, by virtue of the processing module 7, to be displayed on the oscillogram in FIG. 2B in the form of an echo signal 8a.

The time lag between the signal 8 and the signal 8a corresponds to twice the time $\delta T$ taken for the ultrasonic waves to travel through the wall of the tube 1.

It is possible to obtain an approximate value for the total thickness $e_8$ of the jacket corresponding to the thickness of the wall of the duplex tube by assuming that the speeds of propagation of the ultrasonic waves in the metallic core of the Jacket and in the cladding layer are identical.

This method of determination is only approximate, inasfar as the speed of propagation $V_p$ of the longitudinal ultrasonic waves in the cladding material is not identical to the speed of propagation $V_a$ of the ultrasonic waves in the material constituting the core of the duplex tube.

On the other hand, the method of measuring directly the propagation time of ultrasonic waves does not permit the measurement of the thickness of the cladding layer $e_p$, the coefficient of reflection of the acoustic waves at the interface 4 between the cladding layer 3 and the core 2 being very small (generally less than 2%), because the acoustic properties of the materials constituting the cladding layer and the core are extremely similar to each other.

Furthermore, the cladding layer has a small thickness as compared with the total thickness of the wall, with the result that the differences in the propagation times to be taken into account are themselves very small.

Figure 3A:
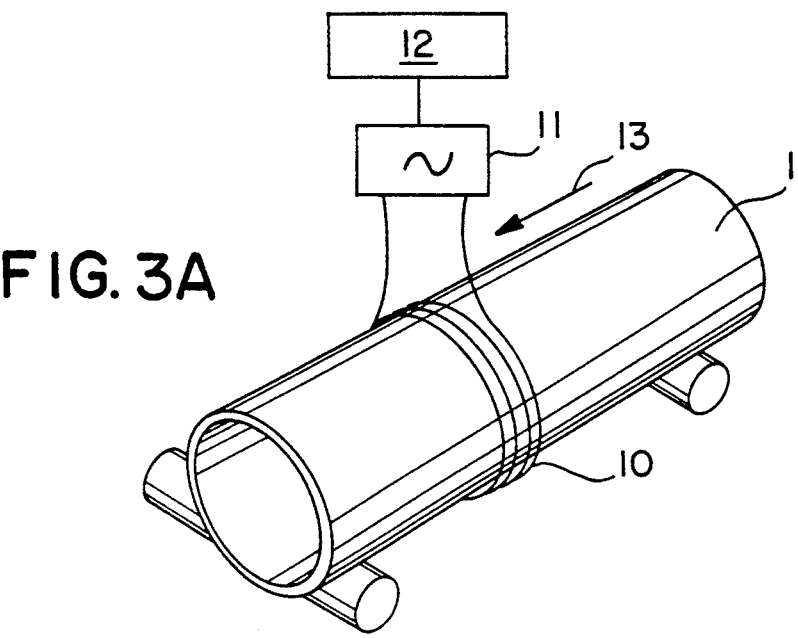
FIGS. 3A, 3B and 3C show three alternative embodiments of a device for measuring, by Foucault currents, the thickness of the covering or cladding layer of a duplex tube.
Figure 3B:
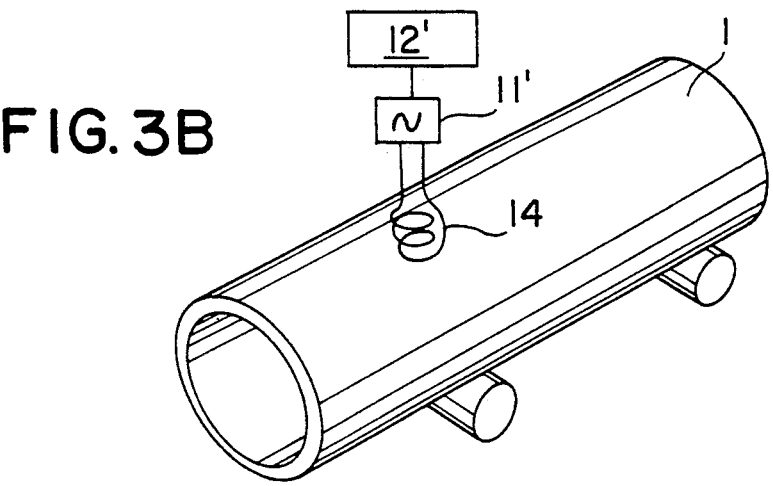
Figure 3C:
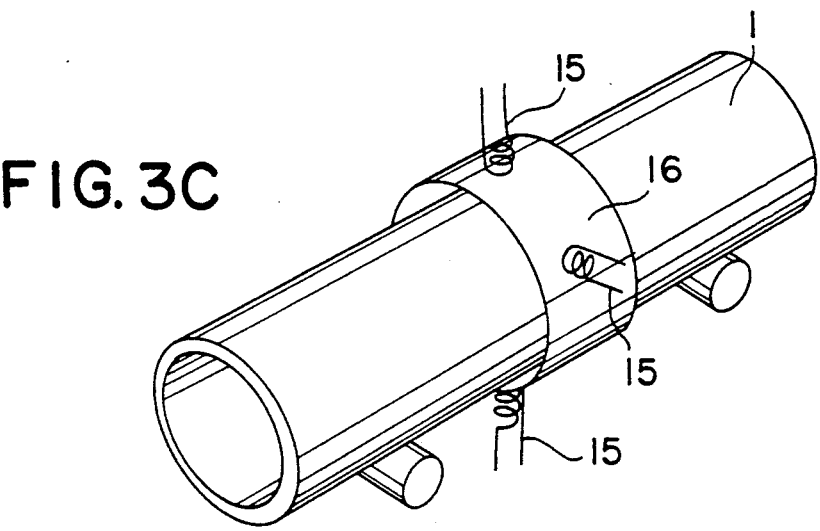

In FIGS. 3A, 3B and 3C, three different embodiments of a Foucault-current device have been shown, permitting the measurement of the thickness of an outer cladding layer of a duplex tube 1 consisting of a metallic core covered with a cladding layer, the metallic core and the cladding layer consisting of two zirconiumalloys containing very small quantities of alloying elements.

Small variations in alloying measurements in lowalloy alloys can give rise to very considerable variations in the electrical conductivity of these alloys.

For example, in the case of zircaloy, which is a zirconium alloy containing tin, a variation of 1% in the tin content gives rise to a variation in conductivity of the order of 50%.

Such variations make it possible to apply the technique of induced currents or Foucault currents in order to check the thickness of a cladding layer whose composition differs from that of the metallic core covered by the cladding layer.

It is possible to use, as shown in FIG. 3A, a coil 10 comprising a certain number of turns surrounding the tube 1.

The coil is supplied by a multi-frequency sinusoidal exciting current via a current source 11 connected to its terminals. The electrical signals corresponding to the induced currents are processed by a a processing unit 12.

In the case of this first embodiment of the device for measurement by Foucault currents, in fact the mean value of the thickness of the cladding is measured, which incorporates the possible variations in thickness at the circumference of the tube, or circumferential variations. The variations in thickness over the length of the coil 10, or axial variations, are likewise incorporated.

According to this principle, the measurement is also sensitive to the centering of the tube within the coil constituting the Foucault-current probe, so that this centering, even if carried out optimally, is likely to reduce the accuracy of the measurement.

A second measurement technique such as that shown in FIG. 3B consists in using a coil 14, the axis of which has a radial direction with respect to the tube 1.

The excitation of the coil by a multi-frequency sinusoidal current, by virtue of a current source 11', and the processing of the signals corresponding to the induced currents by a processing unit 12', are carried out in the same way as in the case of the measurement device shown in FIG. 3A.

The device such as that shown in FIG. 3B makes it possible to carry out a localized measurement of the thickness of the cladding of the tube 1.

As shown in FIG. 3C, it is also possible to use a plurality of coils 15 similar to the coil 14 shown in FIG. 3B and fixed on a common support 16, so that the coils 15, the axes of which extend radially with respect to the tube 1, are arranged about the tube in regularly distributed circumferential positions.

It is thus possible to carry out simultaneously thickness measurements at various points distributed about the circumference of the tube.

It is also clear that it is possible to sweep the surface of the tube, for example by displacing the tube axially with respect to the Foucault-current probe, as shown by the arrow 13 in FIG. 3A.

The frequency of the sinusoidal exciting signal, and the dimensions of the windings (diameter and height) are determined so as to optimize the sensitivity of the measurements to the variations in thickness of the cladding and to minimize the variations of the measurement signals caused by variations in the distance between the coil and the surface of the tube, constituting an air gap.

This air-gap or lift-off effect can be considerably reduced by an appropriate choice of the frequency, as indicated in FR-A-2,534,015.

In order to improve the quality of the measurement and, in particular, in order to take into account possible variations in electrical conductivity of the alloys constituting the core and the cladding of the tubes, this electrical conductivity being very sensitive to the composition of the alloys, it is possible to use, in addition to the main exciting frequency as defined above, one or more auxiliary frequencies intended to compensate for variations in composition on a given tube or within a given batch of tubes or within a given casting operation.

The invention is therefore characterized by the use of a multi-frequency sinusoidal exciting signal having a main frequency and secondary frequencies.

It is possible, in particular, to use a second frequency which is sensitive to the mean variation in conductivity of the alloys constituting the core and the cladding, this second frequency being insensitive, or having a very low sensitivity, to the variations in thickness of the core and of the cladding.

It is also possible to use two auxiliary frequencies, one of which is sensitive to the variation in conductivity of the base material constituting the core while at the same time being very slightly sensitive to variations in conductivity of the cladding and to variations in thickness of the core and of the cladding, and the other of which is sensitive only to variations in conductivity of the cladding.

It is also possible to use a supplementary frequency to carry out measurements and compensations of the lift-off effect.

The probe is excited simultaneously by each of the sinusoidal signals having the frequencies determined in the manner described above, and the phase-measurement and amplitude-measurement signals corresponding to each of the sinusoidal signals of determined frequency are digitized and processed, as indicated above, by a processing module and by data-processing means which make it possible to deduce from these signals the value of the thickness of the cladding.

The measurement of the thickness of the cladding is obtained either by analysis of the phase of the signal corresponding to the Foucault currents, this method having the advantage of being less sensitive to the variations in lift-off, or by combined analysis of the phase and the amplitude of the signals corresponding to the Foucault currents.

In a general manner, the device used for measuring the thickness of the cladding by Foucault currents comprises:
- a checking head containing the Foucault-current probes and ensuring the positioning of these probes on the tube, and the precise guidance of the tube,
- at least one Foucault-current probe fixed on the checking head,
- a source of multi-frequency exciting sinusoidal current,
- mechanical means for driving and accurate guidance of the tubes past the checking head,
- highly accurate means for checking the linear advance of the tubes and for measuring their axial-position, and
- means for the acquisition and the data-processing of the Foucault current measurements carried out.

The obtention of an accurate value for the thickness $e_p$, measured by Foucault currents and measurement of the passage time of a longitudinal ultrasonic wave propagating in the total thickness of the jacket in a direction perpendicular to the surface, as shown in FIGS. 2A and 2B, makes it possible to obtain an accurate value for the total thickness of the Jacket.

This total thickness of the Jacket $e_g$ is given by the formula $e_g = e_p + (\delta t - e_p/V_p) \times V_a$, in which $e_p$ represents the thickness of the cladding measured by Foucault currents, $V_p$ the speed of the longitudinal ultrasonic waves in the cladding material, $V_a$ the speed of the longitudinal ultrasonic waves in the material of the core of the tube, and $\delta t$ the propagation time of the ultrasonic wave in the total thickness of the jacket.

In this expression, $e_p/V_p$ represents the passage time of the ultrasonic wave in the cladding material, $(\delta t - e_p/V_p)$ represents the passage time of the ultrasonic wave in the core of the tube, $(\delta t - e_p/V_p) \times V_a$ represents the thickness of the core, for an axial position of the tube which is perfectly determined by virtue of the means for checking and measuring the axial position.

This calculation is, of course, only valid in the case where the speeds $V_p$ and $V_a$ are sufficiently different give rise to significant errors during the measurement and calculation of the thickness of the tube.

The invention also permits the detection of flaws in cohesion at the interface between the cladding and the core of the tube.

The flaws in cohesion are plane, of negligible thickness and parallel to the surface of the tube.

It would therefore be very difficult to detect these flaws by Foucault currents.

An ultrasonic detection technique is therefore better suited, although the very small depth of the flaw beneath the surface of the tube corresponding to the thickness of the cladding layer (between 80 and 100 μm) constitutes a difficulty in detection of the flaws in cohesion at the interface.

It is possible to use techniques for detection by the reflection of ultrasonic waves which are known per se and which are represented in FIGS. 4A, 5A and 6A and on the corresponding oscillograms of FIGS. 4B, 5B and 6B.

The chief disadvantage of these reflection detection techniques lies in the need to use ultrasonic waves at a very high frequency, for example at a frequency greater than 100 MHz, which corresponds to wave lengths in the zirconium of less than 50 μm.

According to a first reflection detection technique, represented in FIGS. 4A and 4B, ultrasonic waves are emitted in substantially radial directions with respect to the tube, in other words with a substantially normal incidence.

In FIG. 4A, an ultrasonic beam 21 has been shown, reflected on the outer surface of the tube, an ultrasonic beam 22 reflected on a flaw 20 situated at the interface 4 between the cladding layer 3 and the core 2 of the tube, and a beam 23 reflected on the inner surface of the tube, the corresponding echoes 24, 25 and 26 being shown in FIG. 4B.

The echo signal 26 reflected by the inner surface of the tube has a smaller amplitude than the signal 24 reflected by the outer surface of the tube. The time lag between these two echoes corresponds to twice the passage time of the ultrasonic waves in the thickness of the tube.

The echo signal 25 corresponding to a reflection on a flaw 20 at the interface 4 has a smaller amplitude and a very small time lag compared with the signal reflected on the outer surface of the tube because of the very small thickness of the cladding layer 3.

This first method of detection is therefore limited by the fact that the flaw is very close to the outer surface of the tube, and hence by the fact that the corresponding echo 25 can be mixed with the echo 24 which has a large time width due to the effect of the electronic amplification of the ultrasonic signal.

A second method, illustrated by FIGS. 5A and 5B, consists in using a beam of ultrasonic waves 27 with oblique incidence so that this beam is first reflected by the inner surface of the tube, then by the flaw 28 at the interface and again by the inner surface of the tube.

In this case, the echo 29 corresponding to the reflection on the flaw 28 after an initial reflection on the inner surface of the tube, followed by a second reflection on the inner surface of the tube, has a considerable time lag compared with the echo 24.

Similarly, the echo 29 and the immediately following echo 29 reflected by the inner surface of the tube have a small, equivalent amplitude and time width and can therefore be separated easily.

This technique can, however, be difficult to implement depending on the nature of the flaw and insofar as it must be carried out with oblique incidence.

It may also be necessary to use an ultrasonic transducer with a separate emitter and receiver.

A third measuring method is illustrated by FIGS. 6A and 6B.

The checking is carried out from the inside of the tube and the ultrasonic beam is emitted with normal incidence so as to obtain a direct reflection on the flaw 30.

The echo 31 corresponding to the reflection on the flaw 20 has a smaller amplitude and a large time lag compared with the signal reflected by the inner surface of the tube.

Similarly, this echo 31 and the immediately following echo 31' resulting from the reflection on the outer surface of the tube have small, equivalent amplitudes and time widths and can therefore be separated easily.

However, this detection method is difficult to implement in an industrial context, insofar as the checking must be effected from the inside of a tube of small diameter and of great length.

It is thus difficult to obtain checking rates which are sufficient for use of the method on an industrial scale.

Furthermore, the use of ultrasonic waves with very high frequencies has disadvantages in the case of the use of the method in an industrial environment, insofar as this method is sensitive to electronic interference.

FIGS. 7A, 7B, 8A and 8B illustrate a technique for detecting flaws in cohesion at the interface between the cladding layer 3 and the core 4 of a duplex tube 1, by transmission of an ultrasonic wave in the wall of the duplex tube constituting a jacket for a fuel rod, the ultrasonic wave then being reflected on the inner surface of the tube, as can be seen in FIG. 7A which relates to a tube or part of a tube which has no flaw in cohesion.

In this case, the oscillogram shown in FIG. 7B has a bottom echo 36, the amplitude of which, although less than the amplitude of the input echo 35, is considerable.

The application of the method to a sound material therefore results in a virtually integral transmission of the ultrasonic wave at the interface between the cladding layer 3 and the core 2 of the tube. The reflection at the interface 4 is, in fact, negligible insofar as the acoustic impedances of the materials constituting the cladding layer 3 and the core 2 are very similar.

Where a flaw in cohesion 37 exists at the interface 4' between the cladding layer 3' and the core 2' of a duplex tube 1', as shown in FIG. 8A, the ultrasonic wave emitted with a virtually normal incidence with respect to the outer surface of the tube cannot be transmitted, or is transmitted only very partially, at the flaw in cohesion 37 situated at the interface 4'.

The ultrasonic energy is dissipated by the successive reflections in the thickness of the cladding layer 3'.

A highly attenuated, or even non-existent, bottom echo 36' is then obtained.

The input echo 35' is widened and represents the dissipation of the ultrasonic energy by successive reflections in the cladding layer.

The method therefore makes it possible to distinguish very easily a sound material from a material having flaws in the cohesion.

This transmission detection technique can be applied by using a beam of ultrasonic waves, the frequency of which is located at an interval permitting easier implementation of the detection method compared with the reflection detection methods which have been described above.

This range of frequencies can lie, for example, between 10 and 20 MHz. Moreover, it is possible to use the ultrasonic transducer with normal incidence, which has advantages for the ease of implementation of the method.

These conditions correspond in practice to those which are currently used in the case of checking the thickness of the wall of a fuel rod jacket.

In FIG. 9, an ultrasonic transducer, or sensor 40, has been shown which makes it possible to detect flaws in cohesion at the interface of a duplex tube 1.

The sensor 40 is designed as to obtain an optimized focusing of the ultrasonic beam 41.

Since the flaws in cohesion at the interface of the duplex tube 1 are flaws which are elongated in the direction parallel to the axis of the tube and have a surface parallel to the surface of the tube, it is desired to obtain a focal spot 42 of oblong shape, the longitudinal axis of which extends accurately in a direction parallel to the axis of the tube. The surface 43 of the focusing lens of the sensor has the shape of a cylindrical sector, and the optimum adjustment of the focal spot is obtained by adjusting the orientation of the sensor so that the bottom echo (36 in FIG. 7B) has a maximum amplitude.

Furthermore, the sensor must have a wide pass band, which is obtained by high damping. Very narrow echoes are thus obtained and, moreover, the input echo (35 in FIG. 7B) is clearly separated from the bottom echo (36 in FIG. 7B). A better display of the time widening of the input echo (echo 35' in FIG. 8B) upon passage over a flaw in cohesion such as the flaw 37 (FIG. 8A) is also obtained.

The sensor 40 is mounted on a mechanical displacement assembly (not shown), which makes it possible to effect a fine adjustment of the focusing of the sensor, of the alignment of the focal spot with respect to the axis of the tube, of the height of the coupling liquid such as water, in other words the distance between the sensor and the tube, and of the incidence of the beam, and, to achieve an accurate guidance of the tube as it passes by in the direction of its axis beneath the ultrasonic sensor 40.

The invention, in its various embodiments, therefore makes it possible to check simply, quickly and accurately the thickness and the cohesion of the interface of a duplex tube by using simultaneously ultrasonic checking techniques and Foucault-current checking techniques.

The implementation of the device according to the invention can easily be achieved industrially, on a very large number of tubes of great length and of small diameter.

It is possible to use ranges of frequencies of the ultrasonic waves which are different from those which have been mentioned and transducers having a form, a structure and dimensions which are adapted to the tubes to be checked. These transducers or sensors can be associated with mechanical adjustment means of any type.

The tube can be displaced in its longitudinal direction with respect to the sensor by guide means and drive means of any type.

The position of the tube and on the zone being checked can be determined accurately by any suitable means.

It is likewise clear that devices can be used for measuring the thickness of the cladding layer by Foucault currents of a type different from those which have been described.

The processing modules and the data-processing means associated with the ultrasonic checking sensor and with the Foucault-current measuring means can consist of conventional components which digitize and process the signals, calculate the thickness, display the results in any form and indicate the presence of flaws in the form of easily recognizable messages.

Lastly, the invention applies to the checking of any duplex tube used as a jacket element for fuel rods of assemblies for nuclear reactors or in any other fields of industry.

Similarly, these types of checking can be applied even more easily to larger tube diameters and thicknesses; the upper limit is fixed by the Foucault-current technique for measuring the thickness of the cladding, and this limit thickness is generally approximately 2 mm in the case of the abovementioned zirconium alloys.

I claim:

1. Device for checking a thickness and cohesion of an interface of a duplex tube comprising a tubular core made from a first alloy covered with a cladding layer made from a second alloy, a base metal of said first alloy, a base metal of said second alloy being identical to a base metal of said first alloy, said device comprising
   (a) at least one ultrasonic transducer disposed for emitting ultrasonic waves in substantially radial directions with respect to said tube, from outside to inside said tube in said cladding layer and said core of said tube;
   (b) detection and measuring means for detecting reflected ultrasonic waves reflected by surfaces of said tube and for determining propagation times and amplitudes and shape of the reflected ultrasonic waves;
   (c) at least one indication coil connected to supply exciting current to a source of multi-frequency alternating current;
   (d) means for measuring at least one of a phase and an amplitude of eddy currents induced in said tube by said induction coil;
   (e) calculating means for calculating a thickness of said cladding layer from one of said phase and amplitude of eddy currents induced in said tube;
   (f) calculating means for calculating a total thickness of said tube from the measurements of propagation times of said ultrasonic waves and the thickness of said cladding layer; and
   (g) means for analyzing an amplitude and shape of the reflected ultrasonic waves.

2. Device according to claim 1, wherein said exciting coil has turns encircling the tube and arranged successively in an axial direction of said tube.

3. Device according to claim 1, wherein said coil has an axis extending substantially radially of said tube.

4. Device according to claim 1, comprising a plurality of coils having winding axes extending radially of said tube, said coils being fixed in spaced circumferential positions on a support encircling said tube.

5. Device according to claim 1, comprising mechanical means associated with said tube to ensure its axial displacement with respect to said coil.

6. Device according to claim 1, wherein said transducer comprises a focusing lens in the form of a portion of a cylinder, in order to focus a beam of ultrasonic waves at an oblong focal spot having a longitudinal axis parallel to the axis of said tube.

* * * * *